(12) United States Patent
Lim

(10) Patent No.: US 12,357,620 B2
(45) Date of Patent: Jul. 15, 2025

(54) USE OF RIFAXIMIN ON CIRCULATING AGED NEUTROPHILS IN SICKLE CELL DISEASE

(71) Applicant: New York Medical College, Valhalla, NY (US)

(72) Inventor: Seah H. Lim, Hawthorne, NY (US)

(73) Assignee: NEW YORK MEDICAL COLLEGE, Valhalla, NY (US)

( * ) Notice: Subject to any disclaimer, the term of this patent is extended or adjusted under 35 U.S.C. 154(b) by 847 days.

(21) Appl. No.: 17/441,840

(22) PCT Filed: Mar. 23, 2020

(86) PCT No.: PCT/US2020/024205
§ 371 (c)(1),
(2) Date: Sep. 22, 2021

(87) PCT Pub. No.: WO2020/198136
PCT Pub. Date: Oct. 1, 2020

(65) Prior Publication Data
US 2022/0184044 A1    Jun. 16, 2022

Related U.S. Application Data

(60) Provisional application No. 62/822,492, filed on Mar. 22, 2019, provisional application No. 62/964,708, filed on Jan. 23, 2020.

(51) Int. Cl.
| | | |
|---|---|---|
| A61K 31/437 | (2006.01) | |
| A61K 31/17 | (2006.01) | |
| A61K 31/7088 | (2006.01) | |
| A61P 7/06 | (2006.01) | |

(52) U.S. Cl.
CPC ............ *A61K 31/437* (2013.01); *A61K 31/17* (2013.01); *A61P 7/06* (2018.01)

(58) Field of Classification Search
CPC ...... A61K 31/7088; A61K 31/437; A61P 7/06
See application file for complete search history.

(56) References Cited

U.S. PATENT DOCUMENTS

| | | |
|---|---|---|
| 3,773,919 A | 11/1973 | Boswell et al. |
| 4,485,045 A | 11/1984 | Regen |
| 4,544,545 A | 10/1985 | Ryan et al. |
| 2006/0257450 A1 | 11/2006 | Mudumba et al. |
| 2012/0077835 A1 | 3/2012 | Selbo et al. |
| 2015/0164866 A1 | 6/2015 | Randall |

FOREIGN PATENT DOCUMENTS

| | | |
|---|---|---|
| EP | 0058481 A1 | 8/1982 |
| EP | 0102324 A2 | 3/1984 |

OTHER PUBLICATIONS

International Search Report and Written Opinion of the International Searching Authority dated Jun. 16, 2020, corresponding to counterpart International Application No. PCT/US2020/024205; 7 total pages.
New York Medical College, "A Phase II Study of Rifaximin (Xifaxan) for Patients with Sickle Cell Disease (SCD),", Oct. 25, 2018; 1 page.
Bass et al., "Rifaximin Treatment in Hepatic Encephalopathy," The New England Journal of Medicine, vol. 362, No. 12, Mar. 25, 2010; pp. 1071-1081.
Dutta et al., "Intestinal Injury and gut permeability in sickle cell disease," Journal of Translational Medicine, vol. 17, vol. 183, (2019); pp. 1-4.
Hwang et al., "Hepatic uptake and degradation of unilamellar sphyingomyelin/cholesterol liposomes: A kinetic study," Proc. Natl. Acad. Sci., USA, vol. 77, No. 7, Jul. 1980; pp. 4030-4034.
Eppstein, et al., "Biological activity of liposome-encapsulated murine interferon y is mediated by a cell membrane receptor," Proc. Natl. Acad. Sci., USA, vol. 82, Jun. 1985; pp. 3688-3692.
Ahmed et al., "Low Incidence of Hospital-Onset Clostridium difficile Infection in Sickle Cell Disease," New England Journal of Medicine, vol. 380, No. 9, Feb. 28, 2019; 2 pages.
Mullen et al., "Rifaximin is Safe and Well Tolerated for Long-term Maintenance of Remission From Overt Hepatic Encephalopathy," Clinical Gastroenterology and Hepatology, vol. 12, (2014); pp. 1390-1397.
Zhang et al., "Neutrophil ageing is regulated by the microbiome," Nature, Sep. 24, 2015, vol. 525 (7570); pp. 528-532.
Kumar et al., "Applicability of and potential barriers preventing allogeneic stem cell transplant in sickle cell patients treated outside a sickle cell program," Am. J. Hematol., 2018, vol. 93; pp. E150-E152.
Fitzhugh et al., "Cardiopulmonary Complications Leading to Premature Deaths in Adult Patients with Sickle Cell Disease," Am J Hematol., Jan. 2010, vol. 85, No. 1; pp. 1-14.
Langer et al., "Biocompatibility of Polymeric Delivery Systems for Macromolecules," Journal of Biomedical Materials Research, vol. 15, 1981; pp. 267-277.

*Primary Examiner* — Bruck Kifle
(74) *Attorney, Agent, or Firm* — Carter, DeLuca & Farrell LLP; George Likourezos

(57) ABSTRACT

Methods of treatment of sickle cell disease are based on the administration of the antibiotic compound rifaximin.

10 Claims, 9 Drawing Sheets

Clinical Characteristics of Patients

| | |
|---|---|
| Age (year) | |
| Median | 29 |
| Range | 24-56 |
| Gender | |
| Male | 8 |
| Female | 5 |
| SCD type | |
| HbSS | 10 |
| HbS beta thal | 2 |
| HbSC | 1 |
| Hydroxyurea use | |
| Yes | 5 |
| No | 8 |
| Transfusion program | |
| Yes | 0 |
| No | 13 |
| L-glutamine use | |
| Yes | 0 |
| No | 13 |
| Number of VOC needing IOA in the preceding 12 months | |
| Median | 4.5 |
| Range | 2 - 13 |
| Number of days needing IOA in the preceding 12 months | |
| Median | 22.5 |
| Range | 8 - 198 |

FIG. 1

USE OF RIFAXIMIN ON CIRCULATING AGED NEUTROPHILS IN SICKLE CELL DISEASE

CROSS-REFERENCE TO RELATED APPLICATION

This application is a national stage entry of International Application No. PCT/US2020/024205, filed Mar. 23, 2020, which claims benefit and priority to U.S. Provisional Application No. 62/822,492, filed Mar. 22, 2019 and U.S. Provisional Application No. 62/964,708, filed Jan. 23, 2020, which are incorporated herein by reference in their entireties.

TECHNICAL FIELD

The present disclosure provides methods of treatment of sickle cell disease based on the administration of the antibiotic compound rifaximin.

BACKGROUND

Sickle cell disease (SCD) is a group of inherited red blood cell disorders due to abnormal hemoglobin. SCD includes sickle cell anemia (SCA) (HbSS), HbSC, and HbS beta thalassemia. It affects 1 in 400 African Americans and up to 2% of the population in some areas of Africa. The abnormal hemoglobin (HbS) polymerizes (aggregates) under conditions of stress causing the red blood cells to assume a sickle shape. SCD causes significant morbidity and mortality in patients. There is a large therapeutic gap in sickle cell disease. While hydroxyurea reduces acute sickle cell-related events, it does not appear to protect patients from cardiopulmonary complications' the major causes of death in SCD patients (Fitzhugh C D et al., Am. J. Hematol. 2010; 85: 36-40). The long-term effects of newer agents such as crizanlizumab and L-glutamine on the disease course remain to be determined. The only cure currently available for SCD is allogeneic stem cell transplant (allo-SCT); however, many barriers prevent allo-SCT from being readily offered to these patients (Kumar A, et al., Am. J. Hematol. 2018; 93: E150-152). Accordingly, additional therapeutic approaches for treatment of sickle cell disease are needed.

Although red blood cell sickling is a pre-requisite for the development of painful vaso-occlusive crisis (VOC), activated and circulating aged neutrophils (CANs) are pivotal for the pathogenesis of VOC. Activated and CANs adhere to vascular endothelium and form the nidus for sickled red blood cells to aggregate on. CANs in mice are regulated by intestinal microbiota (Zhang et al., Nature 2015 525:528-532). Treatment of SCD mice with an oral cocktail of ampicillin, neomycin, metronidazole, and vancomycin (ANMV) induced reduction in CANs and protected mice from fatal tumor necrosis factor-α-induced VOC (Zhang D, et al. Nature 2015; 525: 528-532). However, it is unclear whether the benefits of the ANMV cocktail were related to the local effects on the intestinal microbiota or to the systemic effects of the absorbed ampicillin and metronidazole. Additionally, long-term use of the ANMV cocktail may not be clinically practical and safe.

SUMMARY

The presently disclosed subject matter provides a method of treating or preventing VOC in SCD in a subject in need thereof. The method includes administering to the subject a therapeutically effective amount of the antibiotic rifaximin. Rifaximin is a minimally absorbed oral antibiotic that has been used long-term in patients with advanced liver disease (Mullen K D et al. Clin Gastroenterol Hepatol. 2014; 12: 1390-1397. e2). Its long-term use is not associated with increased risks for the development of *Clostridium difficile* infection (CDI), an important consideration in order not to abrogate the protective effects from CDI that SCD patients enjoy (Ahmed J et al., New Engl. J. Med. 2019; 380: 887-888).

BRIEF DESCRIPTION OF THE DRAWINGS

Various embodiments of the present disclosure are described herein with reference to the drawings wherein:

FIG. 1 demonstrates the clinical characteristics of the patients accrued to the clinical study.

DETAILED DESCRIPTION

Figure 2:
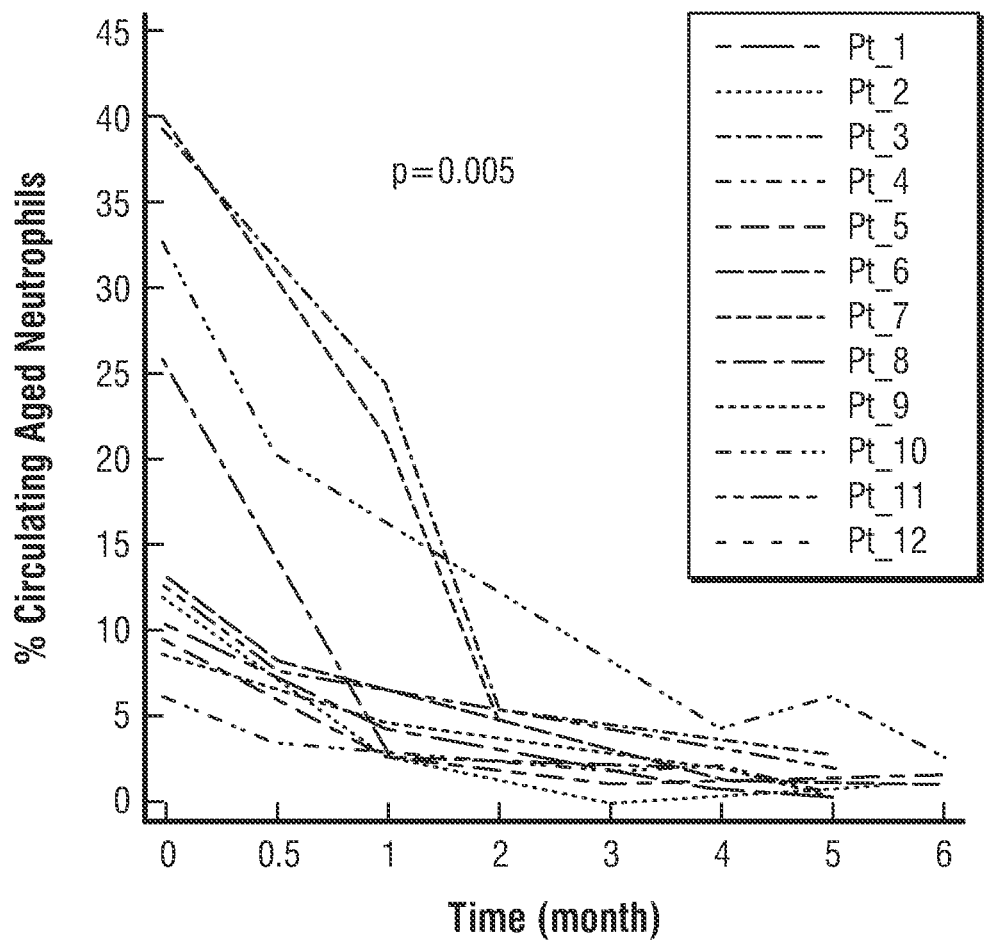
FIG. 2 demonstrates a marked reduction in the circulating aged neutrophils (CANs) following being started on rifaximin. This occurred in all twelve patients and occurred as early as 2-4 weeks after being started on rifaximin.

The presently disclosed subject matter now will be described more fully hereinafter with reference to the accompanying Figures, in which some, but not all embodiments of the presently disclosed subject matter are shown. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the disclosure.

Hemoglobin is a tetrameric protein composed of two pairs of two different subunits. Hemoglobin A (HbA) has α-chain and ß-chain subunits. Hemoglobin S or sickle hemoglobin (HbS) and hemoglobin C (HbC) are "abnormal hemoglobins." HbS results from a substitution of glutamic acid located in a sixth position from an N-terminal of the ß-chain of HbA for valine and HbC for lysine, respectively. SCD, or sickle-cell anemia (or drepanocytosis), is a life-long blood disorder characterized by red blood cells (erythrocytes: RBC) that assume an abnormal, rigid, sickle shape. Sickling decreases flexibility of RBC and results in a risk of various complications, especially painful VOC.

The presently disclosed subject matter provides a method for preventing, or alleviating the symptoms associated with complications of SCD, especially painful VOC, through administration of the antibiotic rifaximin in an effective amount to a subject having a SCD. Rifaximin is a semi-synthetic derivative of rifampin and acts by binding to the beta-subunit of bacterial DNA-dependent RNA polymerase and blocking one of the steps in transcription. This results in inhibition of bacterial protein synthesis and consequently inhibits the growth of bacteria. Rifaximin, sold under the trade name Xifaxan among others, is typically used to treat traveler's diarrhea, irritable bowel syndrome, and hepatic encephalopathy. Rifaximin side effects are generally mild and uncommon, believed to be largely due to low drug absorption from the gut.

In embodiments, the SCD to be treated includes, for example, sickle cell anemia, sickle ß-thalassemia, sickle cell-hemoglobin C disease and any other sickle hemoglobinopathy in which HbS interacts with a hemoglobin other than HbS.

The present disclosure relates to pharmaceutical compositions containing an effective amount of rifaximin for use in prevention and treatment of SCD. The rifaximin may be formulated by methods known to those of skill in the art, and may include, for example, but not limited to solubilizing, diluting, or dispersing substances, such as saline, preservatives, such as benzyl alcohol, absorption promoters, and fluorocarbons.

As used herein, in general, the "effective amount" of rifaximin refers to an amount sufficient to produce the desired effect, such as delivering the amount of active agent. A "therapeutically effective amount" of a therapeutic agent refers to the amount of the agent necessary to elicit the desired biological response. In a specific embodiment, an effective amount is an amount sufficient for prevention or treatment of SCD and associated disorders.

The effective amount of an agent may vary depending on such factors as the desired biological endpoint, the composition of the pharmaceutical composition, the target tissue or cell, the health of the subject to be treated and the like. In some embodiments, the term "effective amount" refers to an amount sufficient to reduce or ameliorate the severity, duration, progression, or onset of a complication of SCD, disorder, or condition, or one or more symptoms thereof.

A "subject" can include a human subject for medical purposes, such as for the treatment of an existing sickle cell condition or disease or the prophylactic treatment for preventing the onset of a sickle cell condition or disease, or an animal subject for medical, veterinary purposes, or developmental purposes. Such animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. Further, a "subject" can include a patient afflicted with or suspected of being afflicted with a condition or disease. Thus, the terms "subject" and "patient" are used interchangeably herein. In one embodiment, the presently disclosed subject matter relates to a method of treating or preventing SCD in a subject in need thereof, the method including administering to the subject a therapeutically effective amount of rifaximin As used herein, "sickle cell disease" means that the subject has sickle cells. As used herein, a "sickle cell" includes a cell which is an abnormal, crescent-shaped erythrocyte that contains sickle cell hemoglobin from a subject with sickle cell disease. "Sickling" includes the process whereby a normal-shaped cell becomes crescent-shaped. Such SCD includes but is not limited to sickle cell anemia, sickle ß-thalassemia, sickle cell-hemoglobin C disease and any other sickle hemoglobinopathy in which HbS interacts with a hemoglobin other than HbS. "Sickle hemoglobinopathy" is an abnormality of hemoglobin which results in sickle cell disease or sickle variants.

As used herein, the term "inhibit" or "inhibits" means to decrease, suppress, attenuate, diminish, arrest, or stabilize the development or progression of a SCD, disorder, or condition by at least 10%, 20%, 40%, 40%, 50%, 60%, 70%, 80%, 90%, 95%, 98%, 99%, or even 100% compared to an untreated control subject. By the term "decrease" is meant to inhibit, suppress, attenuate, diminish, arrest, or stabilize a symptom of a SCD, disorder, or condition. SCD associated symptoms include, but are not limited to, painful VOC, erythrocyte (RBC) sickling, oxygen release, increased HbS polymerization, hemolysis, tissue congestion and organ damage or dysfunction. It should be appreciated that treating a disease, disorder or condition does not require that the disease, disorder, condition or symptoms associated therewith be completely eliminated.

As used herein, the terms "treat," "treating," "treatment," and the like, are meant to decrease, suppress, attenuate, diminish, arrest, the underlying cause of a SCD, disorder, or condition, or to stabilize the development or progression of a SCD, disorder, condition, and/or symptoms associated therewith. The terms "treat," "treating," "treatment," and the like, as used herein can refer to curative therapy, prophylactic therapy, and preventative therapy. Accordingly, as used herein, "treating" means either slowing, stopping or reversing the progression of the SCD, including reversing the progression to the point of eliminating the presence of sickled cells and/or reducing or eliminating the amount of polymerization of hemoglobin, or the amelioration of symptoms associated with sickle cell disease. SCD associated symptoms include, but are not limited to, erythrocyte (RBC) sickling, oxygen release, increased HbS polymerization, hemolysis, tissue congestion and organ damage or dysfunction.

The treatment, administration, or therapy can be continuous or intermittent. Continuous treatment, administration, or therapy refers to treatment on at least a daily basis without interruption in treatment by one or more days. Intermittent treatment or administration, or treatment or administration in an intermittent fashion, refers to treatment that is not continuous, but rather cyclic in nature. Treatment according to the presently disclosed methods can result in complete relief or cure from a SCD, disorder, or condition, or partial amelioration of one or more symptoms of the SCDe, disorder, or condition, and can be temporary or permanent. The term "treatment" also is intended to encompass prophylaxis, therapy and cure.

As used herein, the terms "prevent," "preventing," "prevention," "prophylactic treatment" and the like refer to reducing the probability of developing a SCD, disorder, or condition in a subject, who does not have, but is at risk of or susceptible to developing a SCD, disorder, or condition. Thus, in some embodiments, rifaximin can be administered prophylactically to prevent the onset of a SCD, disorder, or condition, or to prevent the recurrence of a SCD, disorder, or condition.

Pharmaceutical compositions and formulations for use in treatment of SCD include pharmaceutical compositions of rifaximin, alone or in combination with one or more additional therapeutic agents, in a mixture with a physiologically compatible carrier, which can be administered to a subject, for example, a human subject, for therapeutic or prophylactic treatment.

As used herein, "physiologically compatible carrier" refers to a physiologically acceptable diluent including, but not limited to water, phosphate buffered saline, or saline, and, in some embodiments, can include an adjuvant. Acceptable carriers, excipients, or stabilizers are nontoxic to recipients at the dosages and concentrations employed, and can include buffers such as phosphate, citrate, and other organic acids; antioxidants including ascorbic acid, BHA, and BHT; low molecular weight (less than about 10 residues) polypeptides; proteins, such as serum albumin, gelatin or immunoglobulins; hydrophilic polymers, such as polyvinylpyrrolidone, amino acids such as glycine, glutamine, asparagine, arginine, or lysine; monosaccharides, disaccharides, and other carbohydrates including glucose, mannose, or dextrans; chelating agents such as EDTA; sugar alcohols such as mannitol or sorbitol; salt-forming counter-ions such as sodium; and/or nonionic surfactants such as Tween, Pluronics, or PEG. Adjuvants suitable for use with the presently disclosed compositions include adjuvants known in the art including, but not limited to, incomplete Freund's adjuvant, aluminum phosphate, aluminum hydroxide, and alum.

In certain embodiments, the presently disclosed subject matter also includes combination therapies. Additional therapeutic agents, which are normally administered to treat or prevent sickle cell disease, may be administered in combination with rifaximin as disclosed herein. For example, the rifaximin may optionally be administered in conjunction with other compounds (e.g., therapeutic agents) or treatments (e.g., hydroxyurea or blood transfusions) useful in treating sickle cell disease. These additional agents may be administered separately, as part of a multiple dosage regimen, from the composition comprising rifaximin as disclosed herein. Alternatively, these agents may be part of a single dosage form, mixed together with rifaximin, in a single composition.

By "in combination with" is meant the administration of rifaximin, with one or more therapeutic agents either simultaneously, sequentially, or a combination thereof. Therefore, a subject can be administered a combination of rifaximin and one or more therapeutic agents at the same time (i.e., simultaneously) or at different times (i.e., sequentially, in either order, on the same day or on different days), so long as the effect of the combination of both agents is achieved in the subject. When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the rifaximin and one or more therapeutic agents are administered simultaneously, they can be administered to the subject as separate pharmaceutical compositions, each containing either rifaximin or one or more therapeutic agents, or be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times. In such combination therapies, the therapeutic effect of the first administered agent is not diminished by the sequential, simultaneous or separate administration of the subsequent agent(s).

The presently disclosed pharmaceutical compositions can be administered using a variety of methods known in the art depending on the subject and the particular disease, disorder, or condition being treated. More particularly, as described herein, the rifaximin can be administered to a subject for therapy by any suitable route of administration, including orally, nasally, transmucosally, ocularly, rectally, intravaginally, parenterally, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections, intracisternally, topically, as by powders, ointments or drops (including eyedrops), including buccally and sublingually, transdermally, through an inhalation spray, or other modes of delivery known in the art.

When a therapeutically effective amount of the composition(s) is administered orally, it may be in the form of a solid or liquid preparations such as capsules, pills, tablets, lozenges, melts, powders, suspensions, solutions, elixirs or emulsions. Solid unit dosage forms can be capsules of the ordinary gelatin type containing, for example, surfactants, lubricants, and inert fillers such as lactose, sucrose, and cornstarch, or the dosage forms can be sustained release preparations. The pharmaceutical composition(s) may contain a solid carrier, such as a gelatin or an adjuvant. The tablet, capsule, and powder may contain from about 0.05 to about 95% of the active substance compound by dry weight. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition(s) may further contain physiological saline solution, dextrose or other saccharide solution, or glycols such as ethylene glycol, propylene glycol, or polyethylene glycol. When administered in liquid form, the pharmaceutical composition(s) particularly contains from about 0.005 to about 95% by weight of the active substance. For example, a dose of about 10 mg to about 1000 mg once or twice a day could be administered orally.

In another embodiment, the composition(s) of the present disclosure can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the composition(s) in an aqueous or non-aqueous pharmaceutically acceptable solvent which may also contain suspending agents, sweetening agents, flavoring agents, and preservative agents as are known in the art.

For parenteral administration, for example, the composition(s) may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives and buffers as are known in the art. Pharmaceutical compositions for parenteral administration include aqueous solutions of rifaximin. For injection, the presently disclosed pharmaceutical compositions can be formulated in aqueous solutions, for example, in some embodiments, in physiologically compatible buffers, such as Hank's solution, Ringer's solution, or physiologically buffered saline. Aqueous injection suspensions can contain substances that increase the viscosity of the suspension, such as sodium carboxymethyl cellulose, sorbitol, or dextran. Additionally, suspensions of rifaximin may include fatty oils, such as sesame oil, or synthetic fatty acid esters, such as ethyl oleate or triglycerides, or liposomes. For nasal or transmucosal administration generally, penetrants appropriate to the particular barrier to be permeated are used in the formulation. Such penetrants are generally known in the art. For inhalation delivery, the agents of the disclosure also can be formulated by methods known to those of skill in the art, and may include, for example, but not limited to, solubilizing, diluting, or dispersing substances such as, saline, preservatives, such as benzyl alcohol, absorption promoters, and fluorocarbons. Additional ingredients can be added to compositions for topical administration, as long as such ingredients are pharmaceutically acceptable and not deleterious to the epithelial cells or their function.

When a therapeutically effective amount of the composition(s) is administered by intravenous, cutaneous, or subcutaneous injection, the compound is particularly in the form of a pyrogen-free, parenterally acceptable aqueous solution or suspension. The preparation of such parenterally acceptable solutions, having due regard to pH, isotonicity, stability, and the like, is well within the skill in the art. A particular pharmaceutical composition for intravenous, cutaneous, or subcutaneous injection may contain, in addition to the active agent(s), an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition(s) of the present disclosure may also contain stabilizers, preservatives, buffers, antioxidants, or other additives known to those of skill in the art. As noted, particular amounts and modes of administration can be determined by one skilled in the art. One skilled in the art of preparing formulations can readily select the proper form and mode of administration, depending upon the particular characteristics of the composition(s) selected, and other relevant circumstances using formulation technology known in the art, described, for example, in Remington: The Science and Practice of Pharmacy, $21^{st}$ ed. I.

In some embodiments, the presently disclosed pharmaceutical compositions can be administered by rechargeable or biodegradable devices. For example, a variety of slow-release polymeric devices have been developed and tested in vivo for the controlled delivery of drugs. Suitable examples of sustained release preparations include semipermeable polymer matrices in the form of shaped articles, e.g., films or microcapsules. Sustained release matrices include polyesters, hydrogels, polylactides (U.S. Pat. No. 3,773,919; EP 58,481), copolymers of L-glutamic acid and gamma ethyl-L-glutamate (Sidman et al., Biopolymers 22:547, 1983), poly (2-hydroxyethyl-methacrylate) (Langer et al., J. Biomed. Mater. Res. 15:167, 1981; Langer, Chem. Tech. 12:98, 1982), ethylene vinyl acetate (Langer et al., Id), or poly-D-(−)-3-hydroxybutyric acid (EP 133,988A). Sustained release compositions also include liposomally entrapped rifaximin, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy. Such materials can include an implant, for example, for sustained release of the rifaximin.

The presently disclosed subject matter also includes the use of rifaximin, in the manufacture of a medicament for SCD. Regardless of the route of administration selected, the rifaximin pharmaceutical compositions are formulated into pharmaceutically acceptable dosage forms such as described below or by other conventional methods known to those of skill in the art.

Actual dosage levels of the rifaximin can be varied so as to obtain an amount of the active ingredient that is effective to achieve the desired therapeutic response for a particular subject, composition, route of administration, and disease, disorder, or condition without being toxic to the subject. The selected dosage level will depend on a variety of factors including the route of administration, the time of administration, the rate of excretion, the duration of the treatment, other drugs used in combination with the rifaximin, the age, sex, weight, condition, general health and prior medical history of the patient being treated, and like factors well known in the medical arts.

A physician or veterinarian having ordinary skill in the art can readily determine and prescribe the effective amount of the rifaximin-containing pharmaceutical composition required. For example, the physician or veterinarian could start doses of the rifaximin lower than that required to achieve the desired therapeutic effect and gradually increase the dosage until the desired effect is achieved. Accordingly, the dosage range for administration will be adjusted by the physician as necessary. It will be appreciated that an amount of rifaximin required for achieving the desired biological response, e.g., treatment or prevention of sickle cell disease, may be different from the amount of rifaximin effective for another purpose.

In general, a suitable daily dose of rifaximin will be that amount of the drug that is the lowest dose effective to produce a therapeutic effect. Such an effective dose will generally depend upon the factors described above. Generally, doses of rifaximin will range from about 50 mg to about 1000 mg per 12 hours. In certain embodiments, the dosage is between about 200 mg and about 800 mg. In certain embodiments the dosage is between about 300 mg and about 600 mg per 12 hours. For example, in certain embodiments, a dose can be about 200, 250, 300, 350, 400, 450, 500, 550, 600, 650, or 700 mg per 12 hours. In a specific, non-limiting embodiment, the dose is about 550 mg per 12 hours.

Effective dosages may also be determined based generally on the weight of the subject to be treated. In certain embodiments, the doses of rifaximin will range from 1 mg/kg to about 15 mg/kg per 12 hours, about 3 mg/kg to about 10 mg/kg per 12 hours, or about 4 mg/kg to about 9 mg/kg per 12 hours. For example, in certain embodiments, a dose can be about 3 mg/kg, 3.5 mg/kg, 4.0 mg/kg, 4.5 mg/kg, 5 mg/kg, 5.5 mg/kg, 6 mg/kg, 6.5 mg/kg, 7 mg/kg, 7.5 mg/kg, 8.0 mg/kg, 8.5 mg/kg, 9.0 mg/kg, 9.5 mg/kg or 10 mg/kg per 12 hours. In a specific, non-limiting embodiment, the dose is between 7.5 mg/kg and about 8 mg/kg per 12 hours.

If desired, the effective daily dose of the rifaximin can be administered as two, three, four, five, six or more sub-doses administered separately at appropriate intervals throughout the day, optionally, in unit dosage forms.

In an embodiment, pharmaceutical compositions containing rifaximin are provided for use in a method of treating or ameliorating the symptoms a SCD disorder or condition in a subject. Such pharmaceutical compositions for use in the method of treating or ameliorating the symptoms a SCD disorder or condition in a subject includes treatment of sickle cell anemia, sickle ß-thalassemia, sickle cell-hemoglobin C disease and any other sickle hemoglobinopathy in which HbS interacts with a hemoglobin other than HbS.

In an embodiment, the pharmaceutical compositions for use in a method of treating or ameliorating the symptoms a SCD disorder or condition in a subject include those wherein the dose of rifaximin is from (i) about 50 mg to about 1000 mg per 12 hours, (ii) from about 200 mg to about 800 mg per 12 hours, or (iii) from about 300 mg to about 600 mg per 12 hours. In an embodiment, the dose of rifaximim is from about 200, 250, 300, 350, 400, 450, 500, 550, 600, 650, or 700 mg per 12 hours. In an embodiment, the dose of rifaximin is about 550 mg per 12 hour.

In an embodiment, the pharmaceutical compositions for use in a method of treating or ameliorating the symptoms a SCD disorder or condition in a subject include those wherein the dose of rifaximin is (i) from about 1 mg/kg to about 15 mg/kg per 12 hours, (ii) from about 3 mg/kg to about 10 mg/kg per 12 hours, or (iii) from about 4 mg/kg to about 9 mg/kg per 12 hours. In an embodiment, the dose of rifaximin is about 3 mg/kg, 3.5 mg/kg, 4.0 mg/kg, 4.5 mg/kg, 5 mg/kg, 5.5 mg/kg, 6 mg/kg, 6.5 mg/kg, 7 mg/kg, 7.5 mg/kg, 8.0 mg/kg, 8.5 mg/kg, 9.0 mg/kg, 9.5 mg/kg, or 10 mg/kg per 12 hours. In an embodiment, the dose of rifaximin is between 7.5 mg/kg and about 8 mg/kg per 12 hours.

The presently disclosed compositions of rifaximin can be assembled into kits or pharmaceutical systems for use in treating or preventing SCD. In some embodiments, the presently disclosed kits or pharmaceutical systems include rifaximin in unit dosage form. In further embodiments, the rifaximin can be present together with a pharmaceutically acceptable solvent, carrier, excipient, or the like, as described herein.

In some embodiments, the presently disclosed kits include one or more containers, including, but not limited to a vial, tube, ampule, bottle and the like, for containing the rifaximin. The one or more containers also can be carried within a suitable carrier, such as a box, carton, tube or the like. Such containers can be made of plastic, glass, laminated paper, metal foil, or other materials suitable for holding medicaments.

The presently disclosed kits or pharmaceutical systems also can include associated instructions for using rifaximin containing compositions for treating of SCD. In some embodiments, the instructions include one or more of the following: a description of pharmaceutical composition containing rifaximin; a dosage schedule and administration for treating or preventing SCD; precautions; warnings; indications; counter-indications; overdosage information; adverse reactions; animal pharmacology; clinical studies; and references. The instructions can be printed directly on a container (when present), as a label applied to the container, as a separate sheet, pamphlet, card, or folder supplied in or with the container.

EXAMPLE 1

Rifaximin is a minimally absorbed oral antibiotic and it fits the required safety profile. It has been used long-term in patients with advanced liver disease (Mullen K D et al. Clin Gastroenterol Hepatol. 2014; 12: 1390-1397. e2). Its long-term use is not associated with increased risks for the development of *Clostridium difficile* infection (CDI), an important consideration in order not to abrogate the protective effects from CDI that SCD patients enjoy (Ahmed J et al., New Engl. J. Med. 2019; 380: 887-888).

To determine whether rifaximin was capable of reducing CANs in SCD, 13 patients (eight males and five females) with SCD were accrued to a clinical trial. (ClinicalTrials.gov Identifier: NCT03719729). Their clinical characteristics are shown in FIG. 1. There were eight males and five females. Ten patients had HbSS, two HbSß⁰thal, and one HbSC. Their median age was 29 years (range 24-56). The median number of VOC in the previous 12 months was 4.5 (range 2-13) and number of days needing intravenous opioid analgesia (IOA) was 25.5 days (range 8-198). In 12 of the 13 patients, the VOC was in the form of musculo-skeletal pain typical in distribution for the VOC that normally affected individual patients and in one patient, the VOC was predominantly in the form of recurrent priapism. Five of the patients were already taking hydroxyurea and none L-glutamine or on a transfusion program. Six patients were taking oral opioid at home for chronic pain. The study ran between November 2018 and early August 2019, covering the winter months when most of the patients reported having most frequent VOC. One patient did not start rifaximin because he did not keep his appointment despite giving consent. In all twelve evaluable patients, rifaximin (550 mg twice a day for six months) was started during the winter months. CANs were measured by multicolor flow cytometry. Neutrophils were gated by Gr-1$^{hi}$ CD115$^{lo}$ SSC$^{hi}$ and CANs by CD62L$^{lo}$ CXCR4$^{hi}$ within the neutrophil population.

There was a dramatic reduction in CANs after 2-4 weeks of rifaximin therapy (median 12.65% [range 6.07-40.05] vs 4.55% [range 2.63-20.25]) (two-tailed p=0.0036) (FIG. 2). CANs continued to decrease at the three-month time-point in the two patients whose CANs were analyzed. These results, therefore, indicate rifaximin's ability to reduce CANs in humans and support the concept that the local effects on intestinal microbiota contribute to the beneficial effects of the ANMV cocktail.

Figure 3:
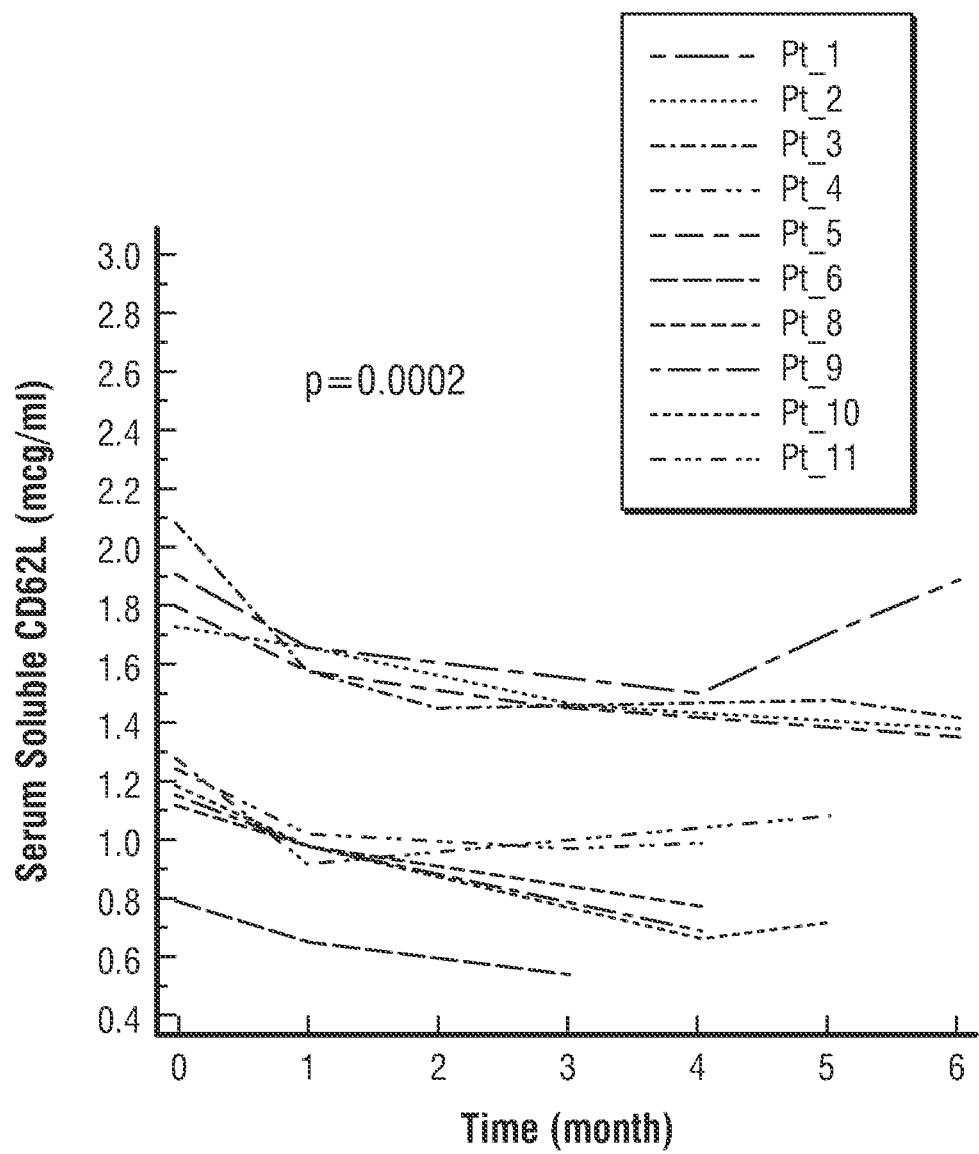
FIG. 3 demonstrates a drop in the serum CD62L, a marker of neutrophil activation following rifaximin treatment.

Both CANs and activated neutrophils are pivotal for the pathogenesis of painful sickle cell VOC. In addition to reducing the CANs, SCD subjects who were treated with rifaximin also showed reduced baseline activated neutrophils, as measured by a significant drop in the serum CD62L, a marker of neutrophil activation (FIG. 3).

Figure 4:
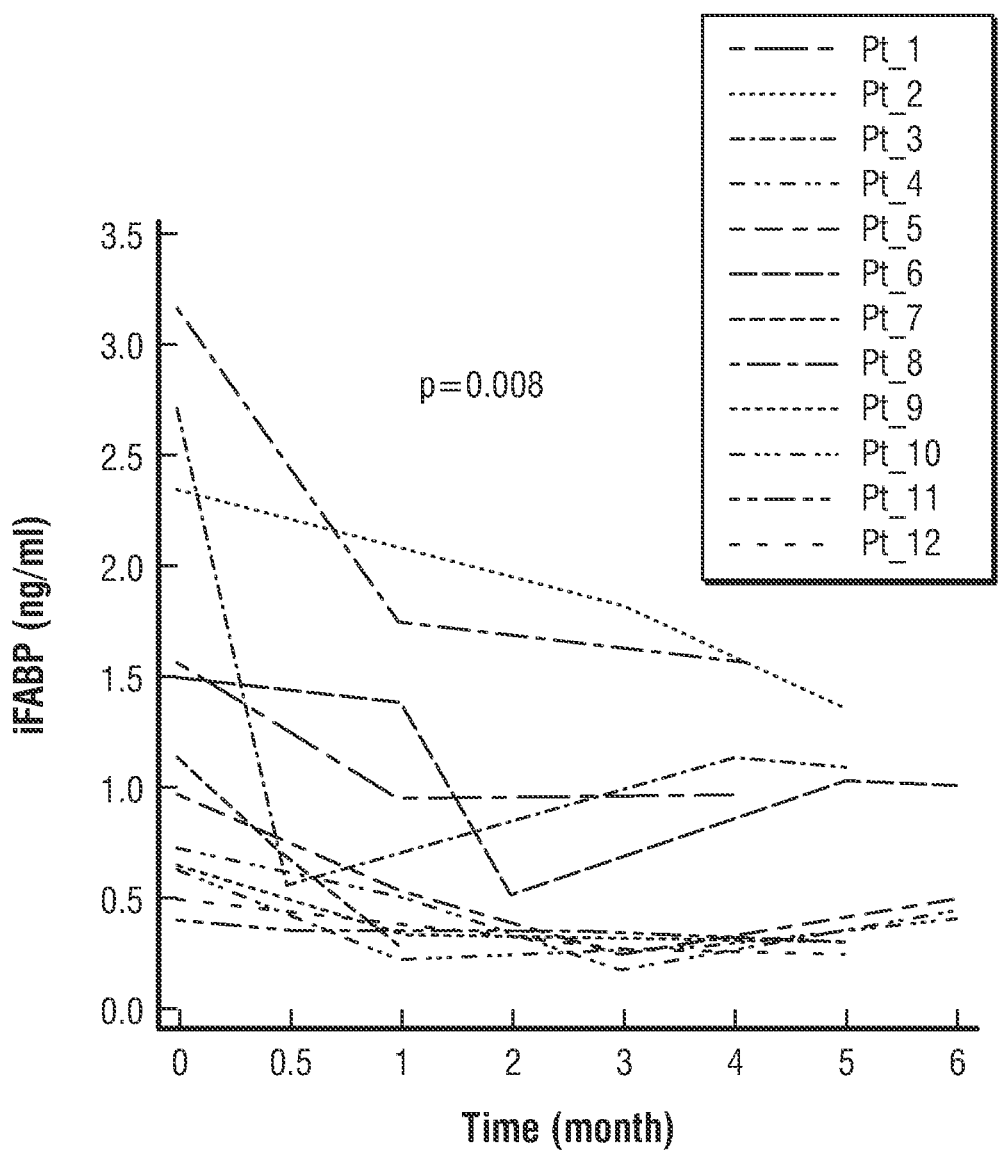
FIG. 4 demonstrates that following rifaximin therapy, the serum iFABP in all the treated patients dropped significantly to levels comparable to controls without SCD.

Evidence of intestinal injury in SCD has also been previously reported, as measured by the significantly higher levels of serum intestinal Fatty Acid Binding Protein (iF-ABP) compared to controls with similar degrees of anemia (Dutta D et al. J Transl Med 2019; 17: 183). To determine whether rifaximin reduced intestinal injury in SCD, serum iFABP was measured in the 12 SCD who were treated with rifaximin. Following rifaximin therapy, the serum iFABP in all the patients dropped significantly (FIG. 4), to levels comparable to controls without SCD (Dutta D et al. J Transl Med 2019; 17: 183), indicating that rifaximin may either protect SCD subjects from intestinal injury or promotes intestinal repair.

Figure 5:
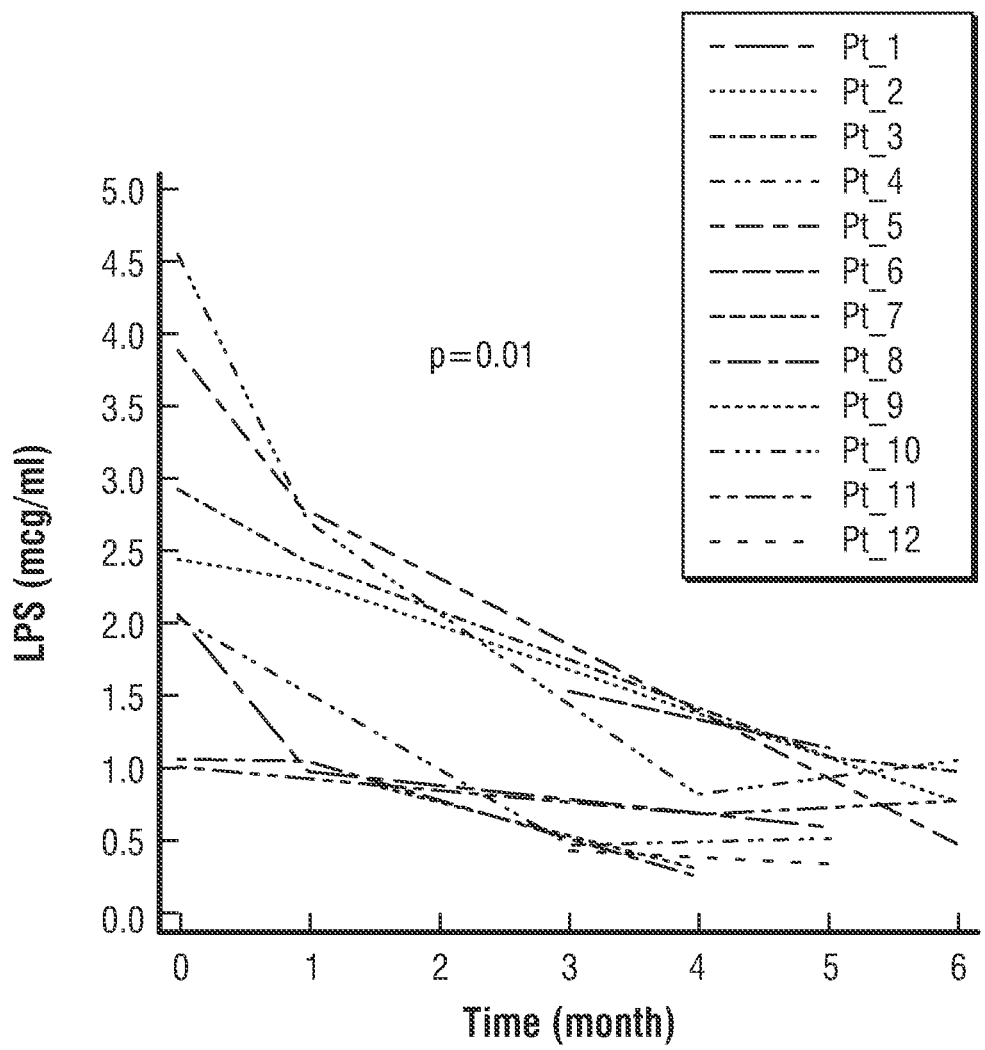
FIG. 5 demonstrates that following rifaximin exposure, the serum LPS levels in all the treated patients dropped significantly compared to pre-treatment levels, to levels comparable to controls without SCD.
Figure 6:
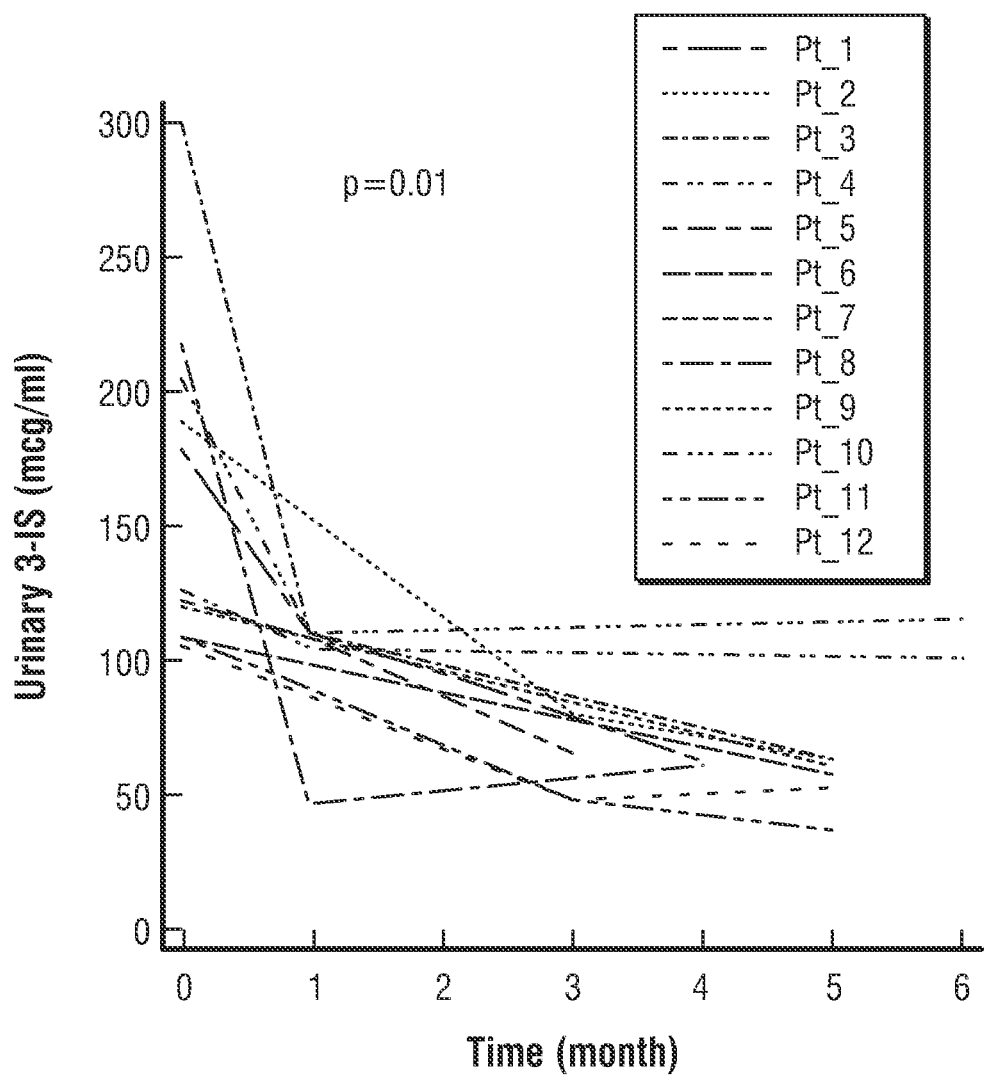
FIG. 6 demonstrates drops in the urinary 3-IS after being started on oral rifaximin.

The effects of rifaximin on translocation of intestinal bacteria/bacterial products in SCD was also studied by measuring changes in the serum lipopolysaccharides (LPS) following rifaximin therapy. It was previously found that SCD subjects showed significantly higher levels of serum LPS (Dutta D. et al, J. Transl. Med. 2019 17:183) that might be responsible for causing the higher CANs and baseline activated neutrophils in these subjects. Following rifaximin exposure, the serum LPS levels in all the patients dropped significantly (FIG. 5), to levels comparable to controls without SCD (Dutta D. et al, J. Transl. Med. 2019 17:183). A reduction in the total intestinal microbial load induced by rifaximin is supported by the observed drop in the urinary 3-IS (FIG. 6).

Figure 7:
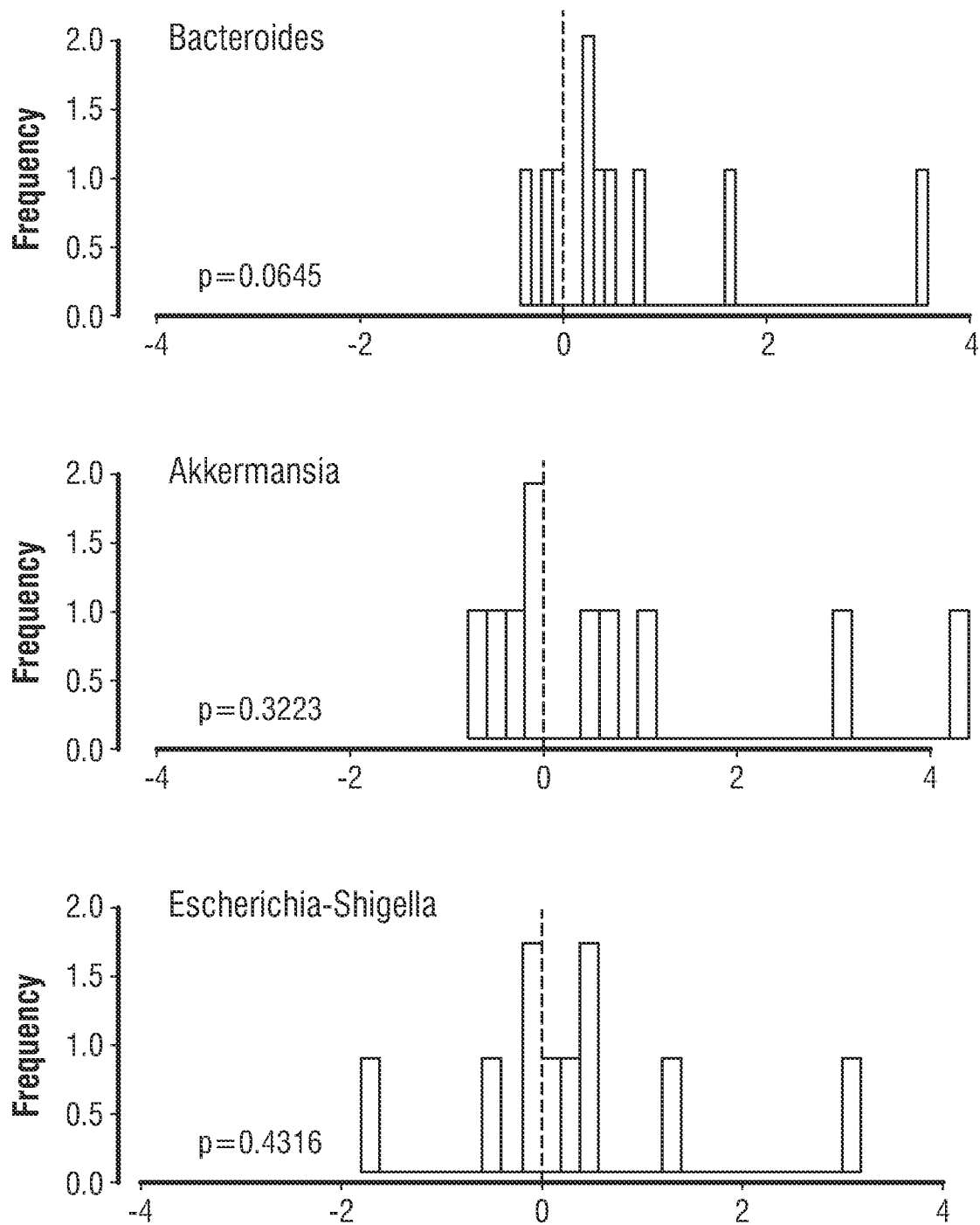
FIG. 7 demonstrates changes in taxonomic abundance in intestinal microbiome after being started on rifaximin. Relative abundances were transformed with the additive log ratio (alr), prior to calculating the difference, to reduce the spurious correlations associated with compositional data. Positive differences signify increased abundance post treatment. Histograms represent the frequency of differences between during and pre-rifaximin treatment alr values, where an increase of abundance during treatment is indicated by a shift of the distribution towards the right. The dashed blue vertical reference line at x=0, indicates no difference due to rifaximin treatment.

16S rRNA analysis of the stool specimens for changes in the intestinal microbiome showed that there was an increase in the abundance of Bacteroides and a trend towards increased abundance in Akkermansia and Escherichia-Shigella (FIG. 7).

EXAMPLE 2

Figure 8:
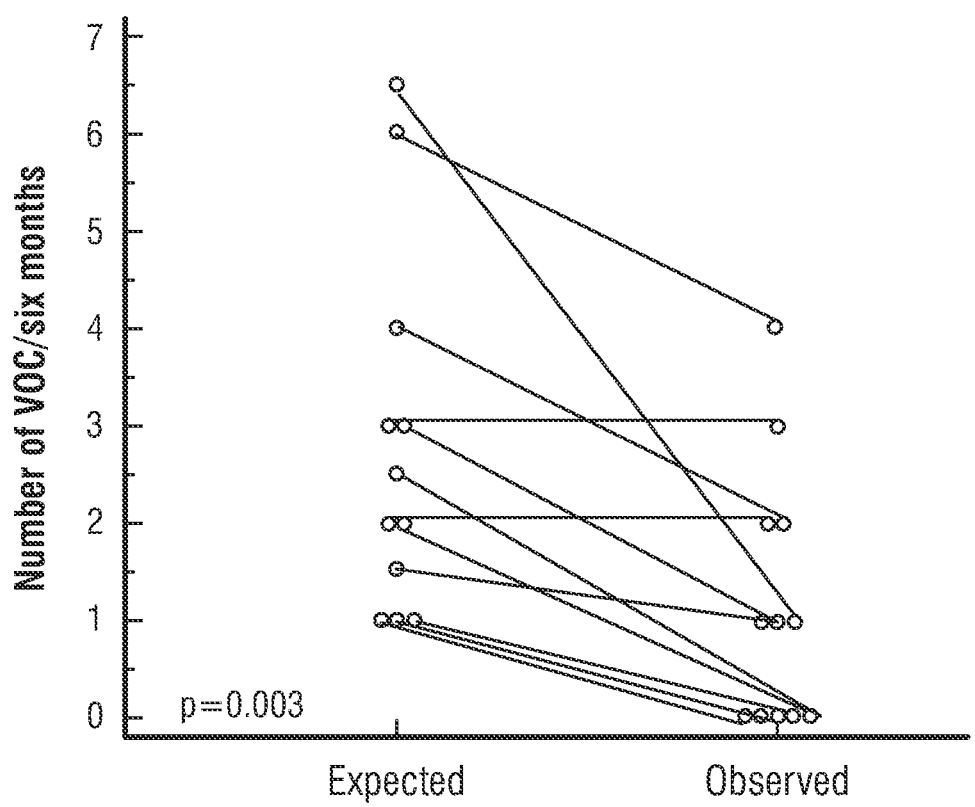
FIG. 8 demonstrates changes in the number of episodes of VOC compared to those expected for a six-month period calculated from the average of the previous 12 months.
Figure 9:
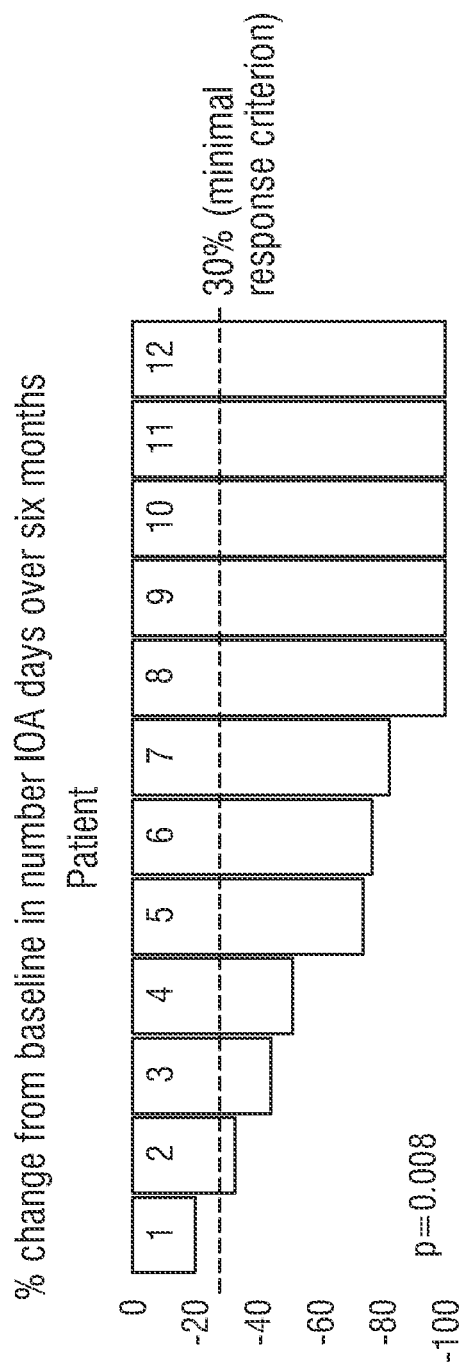
FIG. 9 demonstrates the waterfall plot of changes in the number of days of needing intravenous opioid analgesia compared to the expected number of days for six months estimated from the monthly average of the previous 12 months.

All the laboratory changes induced by clinical use of rifaximin in SCD were translated into clinical benefits. Twelve of the 13 patients accrued to the study were evaluable for response. One patient (HbSC) did not return to be started on the rifaximin after consenting for the study. The remaining 12 patients completed six months of rifaximin. The mean self-reported medication compliance of the intended doses was 86% (range 50-100). The median number of VOC during the study period decreased from the expected 2.25 (range 1-6.5) per 6 months to 1 per 6 months (range 0-4) (p=0.003) (FIG. 8). The one patient whose VOC was predominantly in the form of priapism did not respond. His self-reported medication compliance was 100%. The median decrease in days needing IOA over the six-month study-period was 9 (range 1-55), and the median % reduction was 82 (range 20-100) (p=0.008) (FIG. 9). Total number of days needing IOA was reduced from the expected 254 in six months to 98 during the study period. Laboratory analyses did not show any significant change in hemoglobin, white cell counts, serum lactate dehydrogenase, bilirubin, or haptoglobin due to rifaximin therapy. Rifaximin was well tolerated. Reported adverse events: 1 case of self-limiting probable viral gastroenteritis (culture negative, C. diff negative by PCR) and 2 cases of increased thirst. Slight nausea was common in the first week.

Quality of Life (QoL) survey using the FANTLC questionnaire was carried out before starting rifaximin and repeated 1 and 3 months after rifaximin. Four aspects of QoL issues were examined: Physical well-being, Social well-being, Emotional well-being, and Functional well-being. The scores for response for each of the question were on a scale of 0-4 (0=not at all; 4=very much). As a group, the median score for response to the question "I have pain" decreased from 3.5 to 2 (p=0.08). When the two patients who reported only slight pain before the study (score of 0 or 1) were excluded from the analysis, the median score decreased from 4 to 3 (p=0.04). Changes in the functional well-being of the subjects was examined. As a group, there was not any significant difference following rifaximin. However, when three subjects were excluded who reported excellent functional well-being even before the study (scores of 3 o 4 for all 7 questions) from the analysis, there was an improvement in the functional well-being of the 9 patients, with the median composite score increased from 14 to 16 (p=0.06). In particular, the median scores to the question "I am able to enjoy life" and "I am enjoying the things I usually do for fun" increased from 2 to 2.5 (p=0.026) and 1 to 2.5 (p=0.048) respectively after three months of rifaximin. No significant change in emotional and social well-being was found following rifaximin therapy.

The results of this study, therefore, indicate that rifaximin can benefit patients, as measured by a decrease in the number of VOCs and days needing IOA, in patients with SCD.

In this study, more than 90% of those consented remained in the study for six months. This high retention rate is likely due to two factors. In addition to telephone calls to the patients, until the patients answered the call, on the morning of their follow-up appointments, text messages were also sent to the patients. The clinical benefits, in terms of less frequent painful VOC and improved QOL, experienced by the patients may also contribute to the high patient retention rate.

Rifaximin was chosen in this study for three reasons. First, rifaximin has an established safety profile for long-term use in patients with liver cirrhosis to prevent hepatic encephalopathy (Bass et al., N Eng. J. Med. 2010 362: 1071-1081). Second, the risks for the development of antibiotic-associated *Clostridium difficile* infection induced by long-term use of antibiotics is likely low since rifaximin also has activities against *Clostridium difficile*. Third, being a minimally absorbed antibiotic, rifaximin provided the opportunity to dissect the effect of reducing intestinal microbial load in SCD from any systemic effect an antibiotic might also have on the disease process. The results of the present study using rifaximin, therefore, support the local effects of an antibiotics in the intestine in modifying the course in SCD.

What is claimed:

1. A method of treating complications of sickle cell disease in a subject in need thereof, the method comprising administering to the subject a therapeutically effective dose of rifaximin.

2. The method of claim 1, wherein the sickle cell disease is HbSS, HbSC, or HbSßthal⁰.

3. The method of claim 1, wherein the complications of sickle cell disease include vaso-occlusive crises (VOC).

4. The method of claim 1, further comprising the administration of hydroxyurea and/or an additional anti-SCD agents.

5. The method of claim 1, wherein the dose of rifaximin is from (i) about 50 mg to about 1000 mg per 12 hours, (ii) from about 200 mg to about 800 mg per 12 hours, or (iii) from about 300 mg to about 600 mg per 12 hours.

6. The method of claim 1, wherein the dose of rifaximin is about 200, 250, 300, 350, 400, 450, 500, 550, 600, 650, or 700 mg per 12 hours.

7. The method of claim 6, wherein the dose of rifaximin is about 550 mg per 12 hours.

8. The method of claim 1, wherein the dose of rifaximin is (i) from about 1 mg/kg to about 15 mg/kg per 12 hours, (ii) from about 3 mg/kg to about 10 mg/kg per 12 hours, or (iii) from about 4 mg/kg to about 9 mg/kg per 12 hours.

9. The method of claim 1, wherein the dose of rifaximin is about 3 mg/kg, 3.5 mg/kg, 4.0 mg/kg, 4.5 mg/kg, 5 mg/kg, 5.5 mg/kg, 6 mg/kg, 6.5 mg/kg, 7 mg/kg, 7.5 mg/kg, 8.0 mg/kg, 8.5 mg/kg, 9.0 mg/kg, 9.5 mg/kg, or 10 mg/kg per 12 hours.

10. The method of claim 1, wherein the dose of rifaximin is about 8 mg/kg per 12 hours.

\* \* \* \* \*